United States Patent

Smits et al.

[11] Patent Number: 6,001,954
[45] Date of Patent: Dec. 14, 1999

[54] PROCESS FOR THE MANUFACTURE OF EPOXY COMPOUNDS

[75] Inventors: Jozef Jacobus Titus Smits; Judith Johanna Berendina Walhof, both of Amsterdam, Netherlands

[73] Assignee: Shell Oil Company, Houston, Tex.

[21] Appl. No.: 09/019,545

[22] Filed: Feb. 6, 1998

[30] Foreign Application Priority Data

Feb. 7, 1997 [NL] Netherlands .......................... 97200329

[51] Int. Cl.$^6$ .................... C07C 43/225; C07D 301/026; C08G 59/02
[52] U.S. Cl. ............................ 528/219; 528/95; 528/214; 549/518; 568/641; 568/643; 568/645; 568/649
[58] Field of Search ..................................... 568/641, 643, 568/645, 649; 549/518; 528/214, 219, 95

[56] References Cited

U.S. PATENT DOCUMENTS

| | | | |
|---|---|---|---|
| 2,856,413 | 10/1958 | Malkemus et al. ....................... | 260/348 |
| 4,202,978 | 5/1980 | Fahrenholtz et al. .................... | 544/393 |
| 4,900,801 | 2/1990 | Takata et al. .............................. | 528/87 |
| 4,966,790 | 10/1990 | Iizuka et al. ............................. | 427/386 |

FOREIGN PATENT DOCUMENTS

| | | |
|---|---|---|
| 0047473 | 9/1981 | European Pat. Off. . |
| 0261979 | 3/1988 | European Pat. Off. . |
| 0293237 | 11/1988 | European Pat. Off. . |
| 1122260 | 1/1962 | Germany . |
| 1154808 | 9/1963 | Germany . |
| 57-26677 | 2/1982 | Japan . |
| 57-77682 | 5/1982 | Japan . |
| 61-33180 | 2/1986 | Japan . |
| 2014145 | 8/1979 | United Kingdom . |
| WO 87/03583 | 6/1987 | WIPO . |

OTHER PUBLICATIONS

Organic Syntheses, Collective vol. 2, pp. 292–293, 1943.
(Houben–Weyl) Methoden Der Organischen Chemie, vol. 3, R. Stroh: Herstellung von Chlorverbindungen, pp. 836–837, 1962.
(Houben–Weyl) Methoden Der Organischen Chemie, vol. 3, H. Meerwein: Äther, pp. 79–81, 1965.
Gsan–Zade, Use of the multiple attenuated total internal reflection method for studying the synthesis of epoxy resins, Lakokras. Mater. Ikh Primen., vol. 5, pp. 11–13, 1976.

*Primary Examiner*—Robert E. Sellers

[57] ABSTRACT

Process for the preparation of compounds of the formula

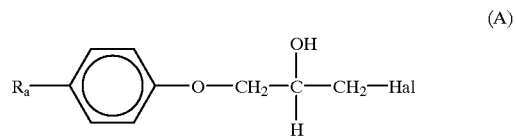

(A)

wherein Hal represents chlorine, bromine or iodine and preferably chlorine, wherein $R_a$ represents hydrogen or a residue comprising one or more additional groups of the formula,

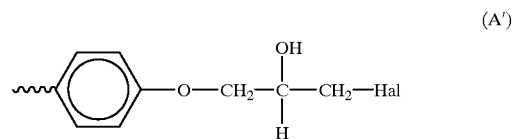

(A')

from compounds

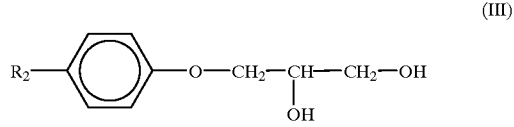

(III)

wherein $R_2$ represents hydrogen or a residue comprising one or more additional groups of the formula

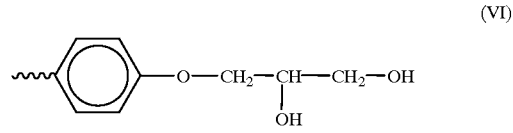

(VI)

by reaction with gaseous hydrogen halide in the presence of a catalytic amount of an organic acid. Epoxy resins are prepared via the reaction of a compound of formula (A) in the presence of a basic compound.

6 Claims, 2 Drawing Sheets

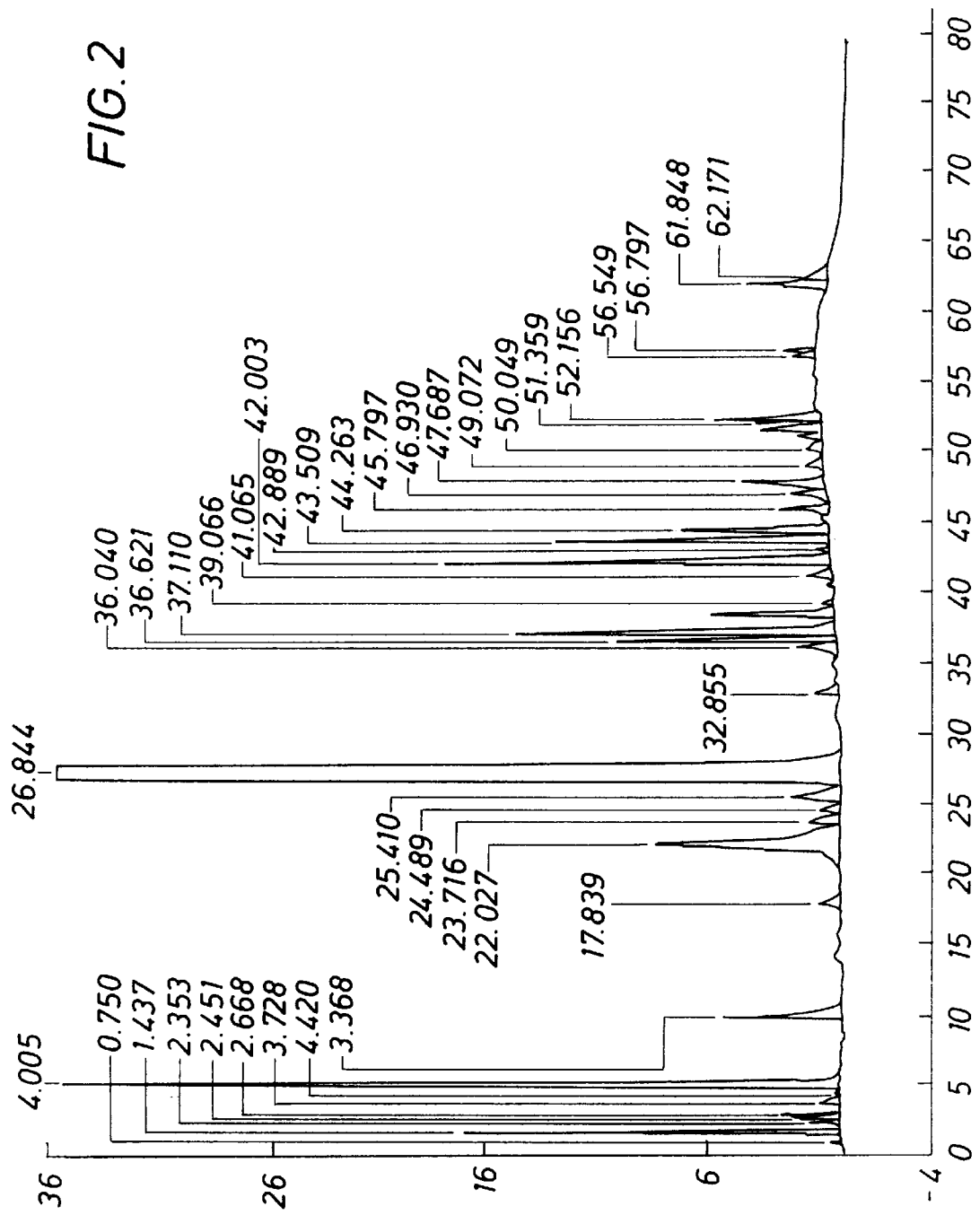

PROCESS FOR THE MANUFACTURE OF EPOXY COMPOUNDS

The invention is relating to a process for the manufacture of epoxy compounds and to a process for the manufacture of intermediates therefor.

BACKGROUND OF THE INVENTION

Epoxy compounds, which are manufactured in a great variety on large industrial scales throughout the world, are used for an extensive scale of end applications, such as the manufacturing of shaped articles, including embedded small electronic components such as semi-conductors or chips and the prepregs for the subsequent manufacture of printed circuits for the electronic industry, coatings including the organic solvent based coatings as well as the more modern aqueous epoxy resin dispersion coatings, and in particular can and drum coatings, composites and laminates showing great flexibility, and the like.

Said starting epoxy compounds were manufactured up to now by means of the starting reagent epihalohydrin and in particular epichlorohydrin, which in its turn was manufactured via allylchloride, prepared from propene and gaseous chlorine.

It will be appreciated that on the one hand, there has been developed in the last decade and in particular in the last five years, an increasing pressure from national or regional governmental regulations and requirements to chemical process industry, in order to drastically reduce possible chlorine emission or even to avoid the use of chlorine completely, and on the other hand, in the current manufacturing processes for chlorination of propene in the gaseous phase there is still a need to improve the yield further and to diminish the high fouling tendency.

Moreover, during the reaction of epihalohydrin with phenolic compounds to form epoxy resin it is not possible to avoid completely that halogen, originating from the epihalohydrin, is intermingled in a resin as a product in the form that the halogen atom is chemically bound to the epoxy resin itself.

As one of the important applications of the epoxy resin is encapsulation of micro electronic material, it will be appreciated that this intermingled halogen liberates as an acid by moisture, during use of the final article for a long period of time and this acid leads to corrosion of a metal material.

One of the alternative manufacturing routes for epoxy resins, proposed in the past was that according the following simplified reaction scheme:

transesterification with e.g. alkylene carbonate ($C_1$–$C_4$ alkyl), cycloallylene carbonate, arylalkylene carbonate or dialkylene carbonate ($C_1$–$C_4$ alkyl) and preferably propylene carbonate +alkyleneglycol, cycloalkylene glycol or arylalkylene glycol, and preferably propylene glycol, wherein $R_1$ represents a residue comprising one or more additional phenol groups, wherein $R_2$, represents a residue comprising one or more additional groups of the formula:

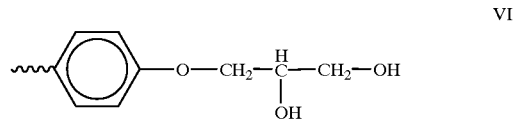

VI wherein $R_3$ represents a residue comprising one or more additional groups of the formula:

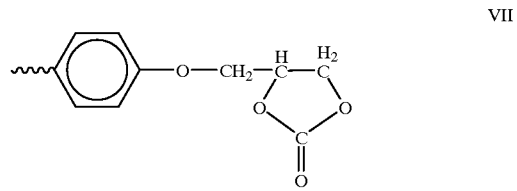

VII and wherein $R_4$ represents a residue comprising one or more additional groups

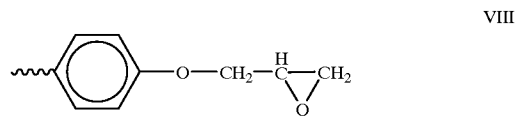

VIII

Although it was already known from e.g. Japanese patent application Sho 61-33180 A, to produce epoxy compounds by decarboxylating a carbonate compound, using as catalyst a combination of an alkali metal halide and of a dihydrogenphosphate of an alkali metal while earlier proposed similar processes were known from e.g. JP-Sho-57-77682 A and U.S. Pat. No. 2,856,413, said route could not be used for economical manufacture of epoxy compounds up to now.

In particular from JP-Sho-61-33180 it will be appreciated that the finally obtained mono epoxy compounds had such a simple molecular structure, that they could be recovered from the initially crude reaction mixture by distillation.

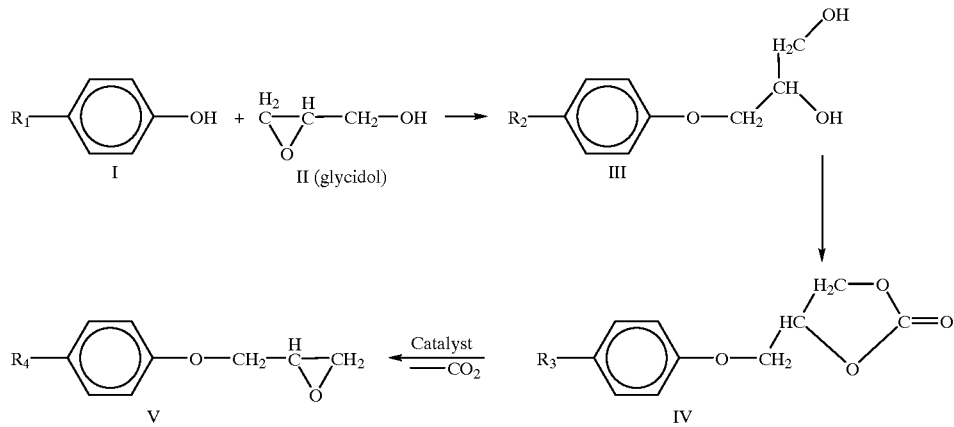

However such a distination has appeared to be not possible for the commercial standard difunctional and multifunctional epoxy compounds aimed at.

Therefore there was still a strong need for improvement of this proposed route to enable industrial scale manufacture of epoxy compounds at all.

BRIEF DESCRIPTION OF THE DRAWINGS

FIG. 2 is a chromatograph of a HPLC analysis for the product obtained in Example H.

Figure 1:
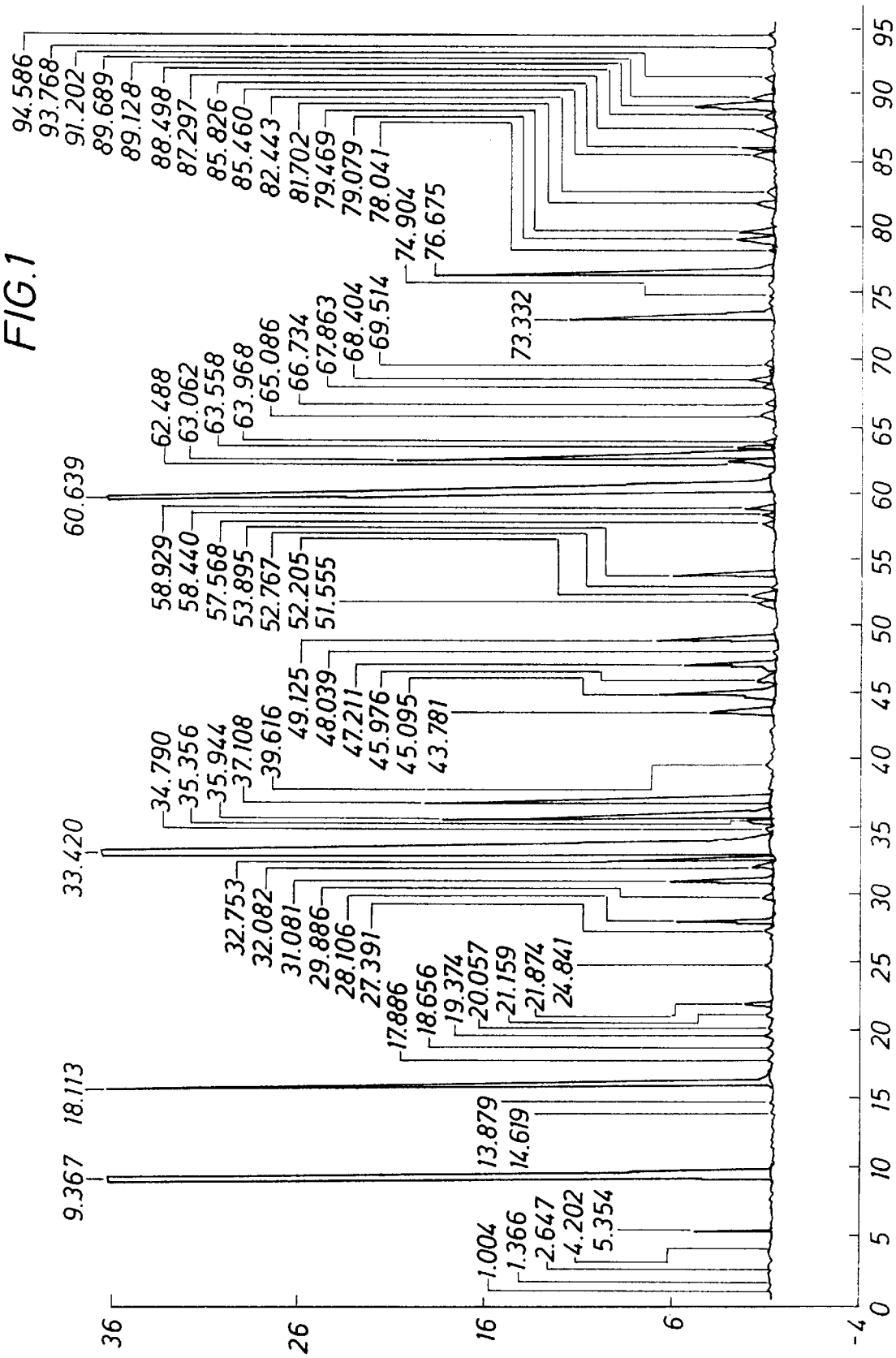
FIG. 1 is a chromatograph of a high-pressure liquid chromatography (HPLC) analysis for an EPIKOTE 828 epoxy resin.

The invention is relating to a process for the manufacture of epoxy compounds characterized by the involvement of significantly less halogen and in particular chlorine gas. As a result of extensive research and experimentation it has now been surprisingly found, that compounds of the formula

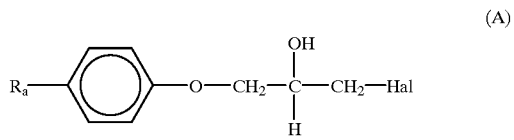

(A)

wherein Hal represents chlorine, bromine or iodine, preferably chlorine, wherein $R_a$ represents hydrogen or a residue comprising one or more additional groups of the formula,

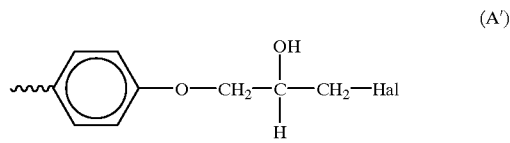

(A')

can be very efficiently prepared from compounds

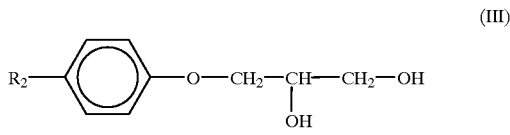

(III)

wherein $R_2$ represents hydrogen or a residue comprising one or more additional groups of the formula

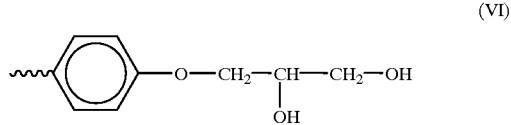

(VI)

by reaction with gaseous hydrogen halide (i.e. hydrogen chloride, hydrogen bromide or hydrogen iodide) and more preferably hydrogen chloride, in the presence of a catalytic amount of an acid of the formula $$R_5-COOH \qquad (IX)$$

wherein $R_5$ represents hydrogen or an alkyl group having from 1 to 10 carbon atoms, optionally substituted by one to three halogen atoms, or a cycloalkyl group having 5 or 6 carbon atoms.

Preferably, the acid of formula (IX) is used in an as much as possible concentrated or glacial form. More preferably glacial acetic acid is used.

The gaseous hydrogen halide or preferably hydrogen chloride to be used for the process of the present invention may contain traces of water up to an amount of up to 5 wt %, but preferably the gaseous HCl will be as dry as possible.

It has been found, that the process of the present invention can only be carried out in an efficent and economical way by the use of gaseous hydrogen halide and preferably HCl, and not with aqueous solutions of HCl, HBr or HJ.

With the term "catalytic amount of acid" is meant an amount of glacial or concentrated acid of from 0.01 to 5 wt % relative to the weight of the starting di-α-glycol of formula III.

Preferably amounts of glacial acetic acid of from 0.02 to 3 wt % and more preferably from 0.02 to 2 wt % are used.

It will be appreciated that the product (of formula A), obtained according this process step., can indeed be almost quantitatively converted into the corresponding epoxy compound of the formula V in the hereinbefore depicted scheme. This process step uses a temperature in the range of from 10 to 120° C. and preferably from 40 to 70° C., in a polar solvent and preferably a ketone such as MIBK (methylisobutyl ketone) or toluene and using a basic compound, such as NaOH, providing epoxy resins with an epoxy group content (EGC) of 5000 mmol/kg or higher. Therefore the process of the present invention provides an economically attractive and efficient. preparation route, starting from a compound of formula I and II to the finally desired epoxy compounds of formula V, instead of the former depicted route, comprising several bottleneck reaction steps, and representing therefore a much less attractive manufacturing process.

It will be appreciated that not only relatively simple compounds, such as

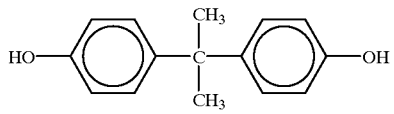

(diphenylpropane or DPP) can be used as starting material of formula I in the above depicted scheme for the preparation of the starting di-α-glycol, but also oligomeric or polymeric compounds, containing a greater number of phenolic groups, which may be converted into the groups of formula (VIII).

I.e. the simple standard epoxy compound of formula

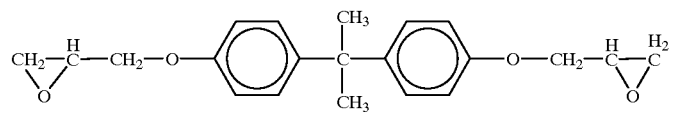

can be prepared according to the process of the present invention, but also a multifunctional epoxy compound, having a much more complicated structure.

However, the use of diphenylolpropane (DPP) as starting material is preferred.

For example in this respect, a great variety of phenol-formaldehyde resins can be used as starting material I (novolac resins).

It was known for a long time to carry out the industrial scale manufacture of compound I starting from a ketone and phenol, providing inexpensive products.

An important representative of compound I, having a rather simple structure is DPP(diphenylolpropane).

Also the reagent II (glycidol) can be regarded as a relative cheap product prepared from propene.

It is true, that from Organic Synthesis, Collective Volume II, p. 292, 1943, it was known for a long time to convert glycerol into 1,3-dichloro-2-propanol with HCl and in the presence of a catalytic amount of glacial acetic acid. However, the yields and selectivities of this simple molecule reaction as far as specified, could certainly not be regarded as an incentive to a person skilled in the art to transform said prior art reaction step to an industrial manufacturing process for the efficient manufacture of epoxy resins.

It will be appreciated that the invention is also relating to a complete integrated manufacturing process for the finally desired epoxy resins, comprising the hereinbefore specified improved process step and starting from a polyphenol compound (I), such as DPP for standard commercial epoxy resins, and glycidol (II).

Accordingly the invention relates to a process for the manufacture of epoxy compounds,; comprising the steps of (a) reaction of a compound

(I)

with a compound

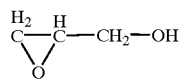
(II)

in the presence of a polar compound and in the presence of a base to form a compound of the formula:

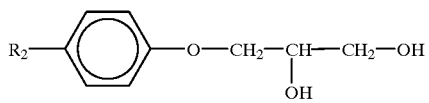
(III)

(b) conversion of the compound of formula (III) obtained in step (a), into a compound of the formula:

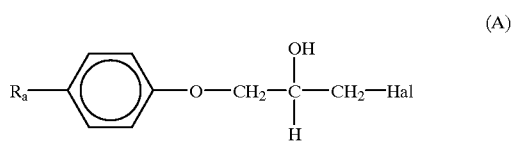
(A)

by reaction with gaseous hydrogen halide, in the presence of a catalytic amount of an acid of the formula

$R_5$—COOH wherein $R_5$ represents an alkyl group, having from 1 to 10 carbon atoms optionally substituted by one to three halogens, or a cycloalkyl group having 5 or 6 carbon atoms, preferably in an as much as possible concentrated or glacial form;

(c) conversion of the compound of formula A into an epoxy compound of formula

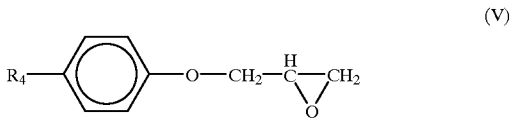
(V)

at a temperature in the range of from 10 to 120° C., in a polar solvent and using an alkali compound.

Preferably in step (a) toluene or a ketone or a mixture of ketone with an alkanol having from 1 to 6 carbon atoms is used and an alkali compound such as NaOH at a temperature of from 30 to 110° C.

More preferably in step (a) an aqueous solution of NaOH (40 to 70 wt %) is used and a temperature of from 60 to 100° C.

Another aspect of the present invention is formed by the final epoxy resins, which are obtainable by the complete manufacturing process as specified hereinbefore and which does contain significantly less intermingled halogen and in particular chlorine, (at most 1500 ppm) and substantially no build-up products (compounds which are normally present in conventionally produced epoxy resins produced from a bisphenol and epihalohydrin of the formula

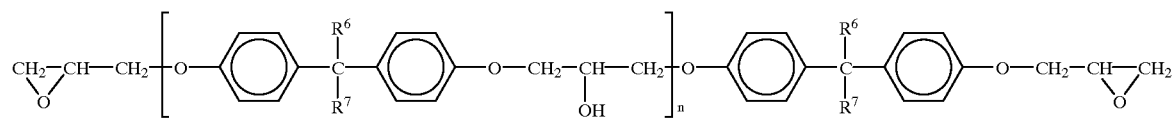

wherein $R_6$ and $R_7$ may represent lower alkyl and preferably methyl, or hydrogen and wherein n=1, n=2 etc.

Said epoxy resins are characterized by HPLC analysis. The chromatogram clearly shows the absence of the so-called build-up products (n=1, n=2 etc.), which are normally present in conventional epoxy resins, prepared from e.g. bisphenol A and epichlorohydrin related to peaks at 60.7 and 76.8, whereas some extra peaks emerge in the chromatogram.

Although it is admitted that this route is not a totally halogen and in particular chlorine free process to epoxy resins, the amount of halogen used has substantially reduced, as in the conventional industrial manufacturing processes a theoretical equivalent of 0.84 ton chlorine per ton epoxy resin is used, whereas in the process of the present invention an amount of only 0.21 ton chlorine per ton epoxy resin is necessary.

Moreover, the present process does not rely on elemental chlorine nor on epichlorohydrin and most likely produces less organic chlorine containing side products.

The invention is further illustrated by the following examples and comparative examples, however, without restricting its scope to these specific embodiments.

EXAMPLE A

Preparation of the bis-chlorohydrin ether of DPP 67 mmnol of the di-α-glycol ether of DPP were charged in a 100 ml three-necked round-bottom flask, equipped with a thermocouple, gas-inlet tube and a reflux condenser. 0.08 Gramn (2 mol %) glacial acetic acid were added and the mixture was heated to 100° C. At this temperature a continuous stream of dry HCl gas was passed through the flask for about 4 hours. The conversion is 100%, the selectivity to the bis-chlorohydrin ether of DPP is about 95%.

EXAMPLE B (Comparative Example)
Preparation of the bis-chlorohvdrin ether of DPP Several attempts were made to produce the bis-chiorohydrin ether of DPP via reaction with aqueous HCl. The reaction was performed in water at different temperatures. It was also tried to perform the reaction in a two phase system (water and an organic solvent). However, all attempts were fruitless. In all cases practically no chlorohydrin ethers were obtained.

EXAMPLE C (Comparative Example)
Preparation of the bis-chlorohydrin ether of DPP The same procedure of Example A was used, but no acetic acid was added. In this case no chlorohydrin ethers were obtained.

EXAMPLE D

Preparation of the bis-bromohydrin ether of DPP

The same procedure as in Example A is used in order to try to convert the di-α-glycol ether of DPP into the corresponding bis-bromohydrin ether of DPP. The conversion is 100%, but the selectivity is significant less, about 45%. The major side reaction is cleavage of the DPP moiety, thus formation of monofunctional compounds occurs. The same side reaction occurs when a 48% aqueous HBr solution was used.

EXAMPLE E

The same procedure as in Example A is used in order to try to convert the di-α-glycol ether of DPP (1) into the corresponding bis-iodohydrin ether of DPP. Again, the conversion is 100%, but the selectivity is significant less, about 40%. The major side reaction is cleavage of the DPP moiety, thus formation of monofunctional compounds occurs. The same side reaction occurs when an aqueous HI solution was used.

EXAMPLE F

The same procedure as in Example A is used in order to try to convert the di-α-glycol ether of DPP (1) into the corresponding bis-fluorohydrin ether of DPP. This reaction does not seem possible. No fluorohydrin compounds could be detected. Instead, cleavage of the DPP moiety occurs. This results in a complex mixtures. For the same reason, aqueous HF solution could not be used.

EXAMPLE G (Comparative Example)
Direct conversion of bis-carbonate ester of DPP in the diglycidylether of DPP Efforts were made to convert the bis-carbonate ester of DPP directly in the diglycidyl ether of DPP, using the procedure described in JP-SHO-61-33180. The reaction was performed at 250° C. and a vacuum was applied. In the beginning of the reaction (first 25 minutes) the lowest pressure obtainable was 4 mbar due to $CO_2$ formation. Hereafter, the vacuum was 1 mbar. The temperature was raised to 270° C. About 50% of the material was distilled. NMR analysis of the distillate showed the presence of ketone end-groups instead of epoxy end-groups. The residue also contained ketone end-groups and oligomeric structures, but no epoxy end-groups.

EXAMPLE H

Preparation of the diglycidylether of DPP

The conversion of the bis-chlorohydrine ether of DPP to an epoxy resin can be achieved via a conventional treatment with base in a suitable solvent and more in particular as follows:

20.63 gram (47.9 mmol) of the bis-chlorohydrine ether of DPP is dissolved in 64 gram MIBK and heated to 85° C. Then, a solution of 6 gram (0.15 mol) NaOH in 34 gram water is added at once, and the mixture is vigorously stirred for 1 hour. After phase separation the MIBK layer is washed twice with 20 grams water. The MIBK is evaporated in vacuo to yield 13.3 gram (83%) of an EPIKOTE 828 type of resin with an epoxy group content (EGC) of 5020 mmol/Kg.

A HPLC analysis of the obtained product provided FIG. 2 using a HP 1090 liquid chromatograph and dissolving 2.0 g of the resin into 20 g of acetonitrile, and using anisole as an internal standard. The analysis was performed using a NOVOPACK C18 column, 15 cm x 3.9 cm, using a flow of 1 ml/min and an injection volume of 1 microlitre and an initial solvent composition, consisting of 75 wt % of water and 25 wt % acetonitrile. A solvent gradient was used.

In 110 minutes the composition changed linear to 6.5% water and 93.5% acetonitrile. At 115 minutes: 0% water and 100% acetonitrile and at 125 minutes: 75% water.

The analysis was performed at 50° C. with UV detection at 275 nm.

Under the same conditions a chromatogram was performed from a standard EPIKOTE 828 resin (FIG. 1).

Alternatively, other bases can be used such as metal hydroxides (for instance KOH, LiOH, $Ca(OH)_2$ or $Mg(OH)_2$), metal carbonates ($Na_2CO_3$, $K_2CO_3$), tertiary amines, $NH_4OH$ etc. Also other solvents can be used, for instance toluene, xylene, MEK, $CH_2Cl_2$, diethylether, etc.

EXAMPLE I

Preparation of the chlorohydrin ether of phenol 15.0 Gram (159 mmol of the α-glycol ether of phenol was charged in a 100 ml three-necked round-bottom flask, equipped with a thermocouple, gas-inlet tube and a reflux condensor. 0.08 Gram (2 mol %) acetic acid was added and the mixture was heated to 100° C. At this temperature a continuous stream of dry HCl gas was passed through the flask for about 4 hours. The conversion is 100%, the selectivity to the chlorohydrin ether of phenol is about 95%.

We claim:

1. A process for the preparation of compounds of the formula

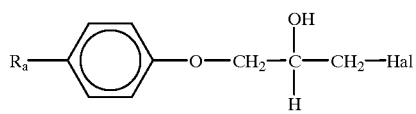
(A)

wherein Hal represents chlorine, bromine or iodine, wherein $R_a$ represents hydrogen or a residue comprising at least one additional group of the formula,

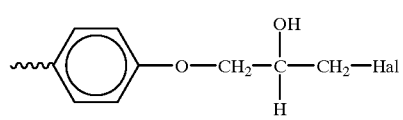
(A′)

by reacting a compound

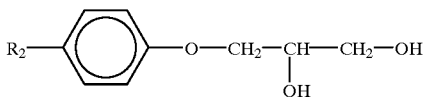
(III)

wherein $R_2$ represents hydrogen or a residue comprising at least one additional group of the formula

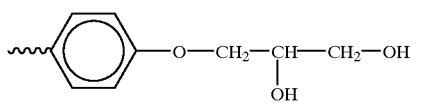
(IV)

with gaseous hydrogen halide in the presence of a catalytic amount of an acid of the formula $$R_5\text{—COOH} \quad (IX)$$

wherein $R_5$ represents hydrogen, an alkyl group, having from 1 to 10 carbon atoms optionally substituted by one to three halogens, or a cycloalkyl group having 5 or 6 carbon atoms.

2. The process of claim 1 wherein the carboxylic acid of formula IX is used in concentrated or glacial form.

3. The process of claim 1 wherein the gaseous hydrogen halide is anhydrous hydrogen chloride.

4. The process of claim 2 wherein the glacial or concentrated acid is used in an amount from 0.01 to 5 wt %, relative to the weight of the starting α-glycol of formula III.

5. The process of claim 1 wherein the acid is glacial acetic acid.

6. The process of claim 1 wherein the compound of formula III is:

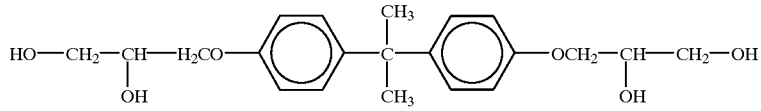

* * * * *